US00PP12389P2

(12) United States Plant Patent
Utecht

(10) Patent No.: US PP12,389 P2
(45) Date of Patent: Feb. 5, 2002

(54) GERANIUM PLANT NAMED 'FISROWI'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/632,243

(22) Filed: Aug. 3, 2000

(51) Int. Cl.[7] ..... A01H 5/00
(52) U.S. Cl. ..... Plt./326
(58) Field of Search ..... Plt./326, 325

(56) References Cited

U.S. PATENT DOCUMENTS

PP10,398 P * 5/1998 Trees ..... Plt./326

OTHER PUBLICATIONS

GTITM UPOVROM Citation for 'Fisrowi' as per QZ PBR 980823; Jun. 15, 1998.*
Fischer Selections 1999/2000 Catalogue featuring Rocky Mountain White ('Fisrowi').
Swiss Application for 'Fisrowi' (Apr. 22, 1999).
European Union Application for 'Fisrowi' (Aug. 17, 1998).
European Union Grant for 'Fisrowi' (Aug. 16, 1999).
German Application for 'Fisrowi' (Aug. 15, 1997).
German Denomination for 'Fisrowi' (Jul. 15, 1998).
German Grant for 'Fisrowi' (Jan. 15, 1999).
Canadian Plant Varieties Journal, Oct. 1999, No. 33, p. 31.

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisrowi', as described and illustrated, and particularly characterized by the combined features of round, semi-double, white flowers, medium-sized, round umbels borne well-above the foliage, fresh-green foliage without, or with only traces of, zonation, early to medium spring flowering response, and vigorous and bushy growth habit.

1 Drawing Sheet

BACKGROUND OF THE INVENTION

The present invention relates to a new and distinct cultivar of geranium plant, botanically known as *Pelargonium zonale*, and hereinafter referred to by the cultivar name 'Fisrowi'.

'Fisrowi' is a product of a planned breeding program which had the objective of creating a new geranium cultivar with white flower color and intense green foliage in combination with moderately vigorous growth.

'Fisrowi' originated from a hybridization made by the inventor, Angelika Utecht, in a controlled breeding program in Galdar, Gran Canaria, Spain, in 1994. The female parent was a hybrid seedling, designated no. 2074/24 (unpatented), which was characterized by white, single-type flowers and dark-green foliage. The male parent was the commercial variety 'Glacis' (unpatented), which was characterized by white, semi-double flowers, rich flower production, medium-green foliage without zonation and medium-tall plant habit.

'Fisrowi' was selected as one flowering plant within the progeny of the stated cross by the inventor, Angelika Utecht, in 1995 in a controlled environment in Galdar, Gran Canaria, Spain.

The first act of asexual reproduction of 'Fisrowi' was accomplished when vegetative cuttings were taken from the initial selection in autumn 1995 in a controlled environment in Galdar, Gran Canaria, Spain, by, or under the supervision of, Angelika Utecht.

Horticultural examination of plants grown from these cuttings, initiated in May 1996 in Hillscheid, Germany, and continuing thereafter, has demonstrated that the combination of characteristics as herein disclosed for 'Fisrowi' are firmly fixed and are retained through successive generations of asexual reproduction.

BRIEF DESCRIPTION OF THE INVENTION

The following traits have been repeatedly observed and are determined to be basic characteristics of 'Fisrowi', which in combination distinguish this geranium as a new and distinct cultivar:

1. white, round, semi-double flowers;
2. semi-spherically shaped inflorescences borne well-above the foliage;
3. bright green foliage without, or with only traces of, zonation;
4. vigorous growth, and bushy, relatively wide plant habit; and,
5. early to medium spring flowering response.

'Fisrowi' has not been observed under all possible environmental conditions. The phenotype of the new cultivar may vary significantly with variations in environment such as temperature, light intensity and day length with any change in the genotype. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fisrowi' are the parental variety 'Glacis' and the variety 'Fisalb' (U.S. Plant Pat. No. 9,761). In comparison to 'Glacis', 'Fisrowi' has similarly colored and shaped inflorescences but with wider upper petals. 'Fisrowi' has slightly more intense green foliage, a wider and more vigorous growth habit and somewhat larger umbels, but it is not quite as floriferous as 'Glacis'. In comparison to 'Fisalb', 'Fisrowi' has more round-shaped flowers with more petals, larger leaves, and distinctly stronger growth habit.

BRIEF DESCRIPTION OF THE DRAWING

The accompanying photographic illustration shows typical flower and foliage characteristics of 'Fisrowi' with colors being as true as possible with an illustration of this type.

DETAILED BOTANICAL DESCRIPTION

The measurements were taken in Langley, British Columbia, Canada, on Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

Classification:

*Botanical.*—A hybrid of the species *Pelargonium zonale* L'Hérit.

*Commercial.*—Zonal geranium, cv. 'Fisrowi'.

Inflorescence:

*Umbel.*—Shape: Semi-spherical. Average diameter: 106 mm. Average depth: 55 mm. Peduncle length: 196 mm. Peduncle color: Light-green, RHS 144 B. Pedicel length: 27 mm. Pedicel color: Light-green, RHS 144 B. Number of flowers per umbel: Approximately 20–25. Lastingness of umbel: Approximately 20–22 days at 18° C.

*Corolla.*—Average diameter: 55 mm. Form: Semi-double. Shape: Nearly round, cup-shaped. Number of petals: 7–9. Size of petals: Upper petals 28–30 mm long, 23–37 mm wide; lower petals 25–27 mm long, 25–27 mm wide. Shape of petals: Obovate, upper end rounded, attenuate base, margin mainly entire, but with slightly crenated tip. Color (general tonality from a distance of three meters): Pure white RHS 155 D. Color of upper petals: RHS 155 D. Markings of upper petals: No markings. Color of lower petals: RHS 155 D. Color of lower surface of petals: RHS 155 D. Number of petaloids: 1–3. Color of petaloids: Upper and lower surfaces white, RHS 155 D. Color of sepals: Light-green, RHS 144 A both outer and inner surfaces. Number of sepals: 5.

*Bud (just before petals unfold).*—Shape: Broad elliptical. Color (sepals): Light-green, RHS 144 A. Color (petals): White to cream, RHS 150 D. Length: 19 mm. Width: 11 mm. Size of sepals: 12–13 mm long, 4–5 mm wide for the largest upper sepal, 3 mm wide for other sepals. Shape of sepals: Linear to lanceolate, acute tip, base truncate, surface weak with pubescence, margin entire.

*Reproductive organs.*—Androecium: 5–7 fertile anthers, white filaments and orange pollen RHS 33A, large quantity of pollen produced. Gynoecium: 5–6-lobed stigma, whitish filament and stigma, one pistil per flower. Fertility/seed set: Spontaneous set of a few seeds may occur; oblong shaped seeds, 4–5 mm in length, brown RHS 177 B.

*Fruit.*—Oblong, approximately 6 mm in length.

*Spring flowering response period.*—In Hillscheid, Germany, in 1999, plants had on average 0.8 flowers opened 8 weeks after planting of rooted cuttings.

*Outdoor flower production.*—Medium to good, the flower count in 1999, in Hillscheid, Germany, indicated about 4 inflorescences per plant in mid-May.

*Durability.*—Good shatter resistance, relatively good heat tolerance and fair rain resistance.

*Lastingness of individual bloom.*—Approximately 9 days at 18° C.

*Fragrance.*—None.

Plant:

*Foliage.*—Form: Kidney-shaped, with open base, weak rounded lobes. Margin: Bicrenated. Texture: Upper surface is slightly velvety. Size of leaf: 97 mm wide, 55–60 mm long. Color of upper surface: Green, varies between RHS 137 C and RHS 137D. Color of lower surface: About RHS 137 D. Color of zonation: Weak, darker-green, about RHS 137 A, and not always visible. Petiole size: 65–75 mm in length, 3 mm in diameter. Petiole color: RHS 144 A.

*General appearance and form.*—Internode length: 10–20 mm. Branching pattern: 8.0 branches.

*Plant size.*—22 cm high, measured from the soil to the surface of the foliage canopy (without the inflorescences), and 41 cm wide.

Disease pest resistance susceptibility: None observed to date.

I claim:

1. A new and distinct cultivar of geranium plant named 'Fisrowi', as described and illustrated.

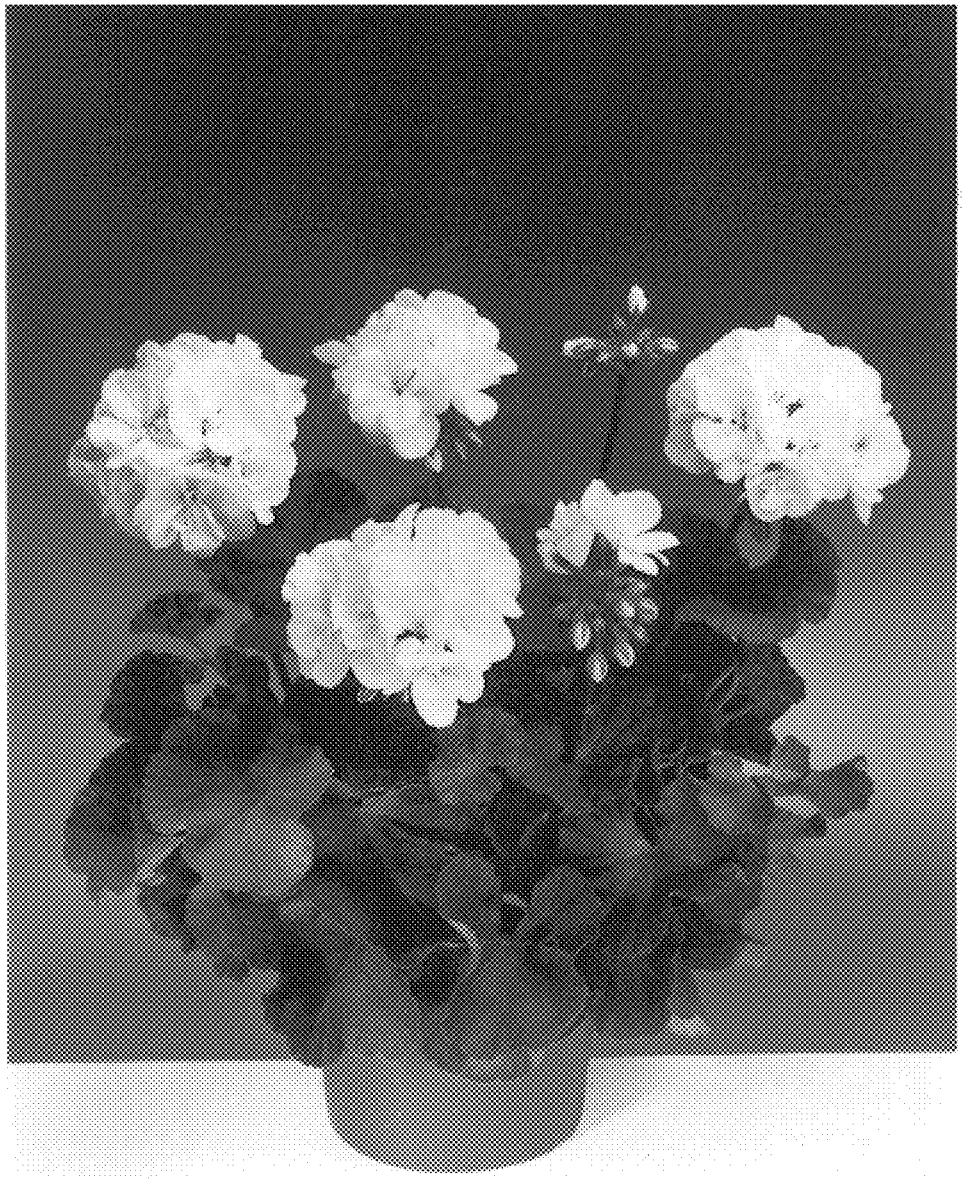

* * * * *